(12) United States Patent
Swinford et al.

(10) Patent No.: US 7,300,462 B2
(45) Date of Patent: Nov. 27, 2007

(54) DEVICE, SYSTEM AND METHOD TO AFFECT THE MITRAL VALVE ANNULUS OF A HEART

(75) Inventors: Gary Swinford, Redmond, WA (US);
Jay N. Wilkins, Belgrade, MT (US);
Cory Williamson, Bozeman, MT (US);
William E. Clem, Bozeman, MT (US);
Erik G. Green, Bozeman, MT (US);
Martin B. Albini, Bozeman, MT (US)

(73) Assignee: Cardiac Dimensions, Inc., Kirkland, WA (US), .

( * ) Notice: Subject to any disclaimer, the term of this patent is extended or adjusted under 35 U.S.C. 154(b) by 0 days.

(21) Appl. No.: 11/276,082

(22) Filed: Feb. 13, 2006

(65) Prior Publication Data

US 2006/0116758 A1 Jun. 1, 2006

Related U.S. Application Data

(62) Division of application No. 10/843,223, filed on May 10, 2004.

(60) Provisional application No. 60/476,870, filed on Jun. 5, 2003.

(51) Int. Cl.
*A61F 2/24* (2006.01)
(52) U.S. Cl. ...................................... 623/2.37; 623/904
(58) Field of Classification Search ............... 623/2.11, 623/2.36–2.37, 904; 606/232
See application file for complete search history.

(56) References Cited

U.S. PATENT DOCUMENTS 3,995,623 A    12/1976    Black et al.

(Continued)

FOREIGN PATENT DOCUMENTS

EP    0893133    1/1999

(Continued)

OTHER PUBLICATIONS

Heartsite.com. Echocardiogram, 1999; p. 1-4. A.S.M. Systems Inc. Available at: http://www.heartsite.com/html/echocardiogram.html. Accessed Jul. 1, 2005.

(Continued)

*Primary Examiner*—Suzette Gherbi
(74) *Attorney, Agent, or Firm*—Shay Glenn LLP

(57) ABSTRACT

A device for modifying the shape of a mitral valve annulus. In one embodiment, the device includes a connector disposed between first and second anchors, the first and second anchors each adapted to be deployed in a coronary sinus adjacent the mitral valve annulus to anchor the device in the coronary sinus; and an actuation element adapted to receive a proximally or distally directed actuation force from an actuator and to transmit the actuation force to the first and second anchors simultaneously. The invention also includes a system for modifying the shape of a mitral valve annulus, including a percutaneous deployment apparatus, including an actuator; and a percutaneous mitral valve annuloplasty device with a connector disposed between first and second anchors, the first and second anchors each adapted to be deployed in a coronary sinus adjacent the mitral valve annulus to anchor the device in the coronary sinus; and an actuation element adapted to receive a distally proximally directed actuation force from the actuator and to transmit the actuation force to the first and second anchors simultaneously. The invention also includes a method of using such devices and systems.

13 Claims, 1 Drawing Sheet

U.S. PATENT DOCUMENTS

| | | |
|---|---|---|
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,441,515 A | 8/1995 | Khosravi et al. |
| 5,474,557 A | 12/1995 | Mai |
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |
| 5,676,671 A | 10/1997 | Inoue |
| 5,733,325 A | 3/1998 | Robinson et al. |
| 5,824,071 A | 10/1998 | Nelson et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,015,402 A | 1/2000 | Sahota |
| 6,027,517 A | 2/2000 | Crocker et al. |
| 6,077,295 A | 6/2000 | Limon et al. |
| 6,077,297 A | 6/2000 | Robinson et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,190,406 B1 | 2/2001 | Duerig et al. |
| 6,210,432 B1 | 4/2001 | Solem et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 * | 6/2002 | Langberg et al. .......... 623/2.36 |
| 6,419,696 B1 | 7/2002 | Ortiz et al. |
| 6,442,427 B1 | 8/2002 | Boute et al. |
| 6,503,271 B2 | 1/2003 | Duerig et al. |
| 6,537,314 B2 | 3/2003 | Langberg et al. |
| 6,569,198 B1 | 5/2003 | Wilson et al. |
| 6,589,208 B2 | 7/2003 | Ewers et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,656,221 B2 | 12/2003 | Taylor et al. |
| 6,676,702 B2 | 1/2004 | Mathis |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,764,510 B2 | 7/2004 | Vidlund et al. |
| 6,776,784 B2 | 8/2004 | Ginn |
| 6,790,231 B2 | 9/2004 | Liddicoat et al. |
| 6,793,673 B2 * | 9/2004 | Kowalsky et al. ......... 623/2.36 |
| 6,797,001 B2 | 9/2004 | Mathis et al. |
| 6,800,090 B2 | 10/2004 | Alferness et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,908,478 B2 | 6/2005 | Alferness et al. |
| 6,949,122 B2 | 9/2005 | Adams et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,090,695 B2 * | 8/2006 | Solem et al. .............. 623/2.37 |
| 7,192,443 B2 * | 3/2007 | Solem et al. .............. 623/2.37 |
| 2001/0018611 A1 | 8/2001 | Solem et al. |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0130730 A1 | 7/2003 | Cohn et al. |
| 2003/0135267 A1 | 7/2003 | Solem et al. |
| 2003/0171776 A1 | 9/2003 | Adams et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0111095 A1 | 6/2004 | Gordon et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0010240 A1 | 1/2005 | Mathis et al. |

| | | |
|---|---|---|
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0065598 A1 | 3/2005 | Mathis et al. |
| 2005/0096666 A1 | 5/2005 | Gordon et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0177228 A1* | 8/2005 | Solem et al. ............... 623/2.36 |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0222678 A1 | 10/2005 | Lashinski et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0116756 A1* | 6/2006 | Solem et al. ............... 623/2.11 |
| 2006/0191121 A1 | 8/2006 | Gordon |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |

FOREIGN PATENT DOCUMENTS

| | | |
|---|---|---|
| EP | 0903110 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| WO | WO 98/056435 A1 | 12/1998 |
| WO | WO 00/44313 A1 | 8/2000 |
| WO | WO 00/60995 A3 | 10/2000 |
| WO | WO 00/74603 A1 | 12/2000 |
| WO | WO 01/00111 A1 | 1/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/049647 A1 | 6/2003 |
| WO | WO 03/059198 A2 | 7/2003 |
| WO | WO 03/063735 A2 | 8/2003 |
| WO | WO 2004/045463 A2 | 6/2004 |
| WO | WO 2004/084746 | 10/2004 |
| WO | WO 2005/046531 | 5/2005 |
| WO | WO 2006/002492 A1 | 1/2006 |

OTHER PUBLICATIONS

Papageorgiou, P., et al. Coronary Sinus Pacing Prevents Induction of Atrial Fibrillation. Circulation. 1997; 96(6): 1893-1898.

Webb, et al. Percutaneous transvenous mitral annuloplasty initial human experience with device implantation in the coronary sinus. Circulation. 2006; 851-855.

Clifton Alferness, et al. U.S. Appl. No. 10/429,225, entitled "Device and method for modifying the shape of a body organ," filed May 2, 2003.

Greg Nieminen, et al. U.S. Appl. No. 10/845,474, entitled "Device and method for modifying the shape of a body organ," filed May 12, 2004.

Greg Nieminen, et al. U.S. Appl. No. 11/275,630, entitled "Tissue Shaping Device," filed Jan. 19, 2006.

Mark Mathis, et al. U.S. Appl. No. 10/994,153, entitled "Body lumen device anchor, device and assembly," filed Nov. 19, 2004.

Mathis, et al; U.S. Appl. No. 11/279,352, entitled "Mitral Valve Annuloplasty Device with Vena Cava Anchor," filed Apr. 11, 2006.

Mathis, Mark; U.S. Appl. No. 11/655,710, entitled "Mitral Valve Device Using Conditioned Shape Memory Alloy," filed Jan. 18, 2007.

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

* cited by examiner

DEVICE, SYSTEM AND METHOD TO AFFECT THE MITRAL VALVE ANNULUS OF A HEART

CROSS-REFERENCE

This application is a Divisional of U.S. Non-Provisional patent application Ser. No. 10/843,223, filed May 10, 2004, which claims the benefit of U.S. Provisional Application No. 60/476,870, filed Jun. 5, 2003, which application is incorporated herein by reference.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a compromised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously affect the geometry of the mitral valve annulus.

Devices of this type generally include an elongated flexible member having a cross sectional dimension for being received within the coronary sinus of the heart and an anchor at each end. When placed in the coronary sinus, the devices reshape the mitral valve annulus, or at least a portion of it, to promote effective valve sealing action and eliminate or reduce mitral valve regurgitation. Device structures and methods of implanting the same are fully described, for example, in copending U.S. patent applications Ser. No. 10,011,867, filed Dec. 5, 2001, titled ANCHOR AND PULL MITRAL VALVE DEVICE AND METHOD, Ser. No. 10/066,426, filed Jan. 30, 2002, titled FIXED LENGTH ANCHOR AND PULL MITRAL VALVE DEVICE AND METHOD, Ser. No. 10/142,637, filed May 8, 2002, titled BODY LUMEN DEVICE ANCHOR, DEVICE AND ASSEMBLY, and Ser. No. 10/331,143, filed Dec. 26, 2002, titled SYSTEM AND METHOD TO EFFECT THE MITRAL VALVE ANNULUS OF A HEART. The disclosures of the foregoing patent applications are incorporated herein by reference.

The foregoing therapy has many advantages over the traditional open heart surgery approach. Since the therapy may be employed in a comparatively noninvasive procedure, mitral valve regurgitation may be treated at an early stage in the mitral regurgitation progression. Further, the therapy may be employed with relative ease by any minimally invasive cardiologist. Still further, since the heart remains completely intact throughout the procedure, the effectiveness of the procedure in reducing mitral valve regurgitation may be readily determined, such as by echocardiography or fluoroscopy. Moreover, should adjustments be deemed desirable, such adjustments may be made during the procedure and before the patient is sent to recovery.

Unfortunately, the human anatomy does impose some obstacles to this recently proposed procedure for treating mitral regurgitation. More specifically, the coronary sinus/ great cardiac vein runs in the atrioventricular groove between the left atrium and left ventricle. The left circumflex artery originates from the left main coronary artery and courses within the atrioventricular groove. One to three large obtuse marginal branches extend from the left circumflex artery as it passes down the atrioventricular groove. These principal branches supply blood to perfuse) the lateral free wall of the left ventricle. In approximately 15% of the population, the left circumflex artery is a dominant source of blood to the left posterior descending artery for perfusing and supporting the viability of the left ventricle. When the circumflex artery is superior to the coronary sinus, the obtuse marginal branches extending towards the ventricular wall may run either underneath the coronary sinus or above the coronary sinus. Hence, when placing a mitral valve therapy device in the coronary sinus/great cardiac vein of a patient, great care must be taken to prevent occlusion of this coronary artery system.

Even when great care is taken to avoid occlusion of the coronary arteries during placement of a prosthetic device in the cardiac venous system, arterial perfusion of the heart may be unacceptably reduced by the device. Copending U.S. patent application Ser. No. 10/366,585, filed Feb. 12, 2003, and titled METHOD OF IMPLANTING A MITRAL VALVE THERAPY DEVICE, the disclosure of which is incorporated herein by reference, discloses a method of optimizing patient outcome while performing a procedure in the venous system of a patient's heart. As described in that patent application, a mitral valve therapy device is placed within the coronary sinus adjacent to the mitral valve annulus of the patient's heart. The effectiveness of the device in reducing mitral valve regurgitation is evaluated, and arterial perfusion of the heart is assessed. Depending on the outcome of the evaluation and assessment, the position of the device may require adjustment or the device may have to be removed. Removal of the device may be advisable, for example, if exchange to a device of different dimension would be more appropriate for that patient.

SUMMARY OF THE INVENTION

The present invention provides a mitral valve therapy device that reshapes the mitral valve annulus. One aspect of the invention is a device for modifying the shape of a mitral valve annulus, including a connector disposed between first and second anchors, the first and second anchors each adapted to be deployed in a coronary sinus adjacent the mitral valve annulus to anchor the device in the coronary sinus; and an actuation element adapted to receive a distally or proximally directed actuation force from an actuator and to transmit the actuation force to the first and second anchors simultaneously to, for example, change the shape of one or both anchors. The device may include a lock adapted to lock the first and second anchors in their deployed configuration, and the lock may be adapted to unlock in response to an unlocking force.

The device may also include a second actuation element adapted to receive a second actuation force from an actuator and to transmit the second actuation force to the first and second anchors simultaneously. The first actuation force may be a proximally directed force and the second actuation force may be a distally directed force, with the first and second actuation elements being adapted to move toward each other in response to the first and second actuation forces. The first and second actuation elements may be a lock adapted to lock the first and second anchors in a deployed configuration.

In some embodiments the device includes an extension extending between the first anchor and the second anchor, with the connector being further adapted to move with respect to the extension in response to the first and second actuation forces. The extension and the connector may each communicate with the first anchor to change the first anchor's shape in response to relative movement between the extension and the connector.

Another aspect of the invention is a system for modifying the shape of a mitral valve annulus including a percutaneous deployment apparatus with an actuator; and a percutaneous mitral valve annuloplasty device including a connector disposed between first and second anchors, the first and second anchors each adapted to be deployed in a coronary sinus adjacent the mitral valve annulus to anchor the device in the coronary sinus; and an actuation element adapted to receive a distally or proximally directed actuation force from the actuator and to transmit the actuation force to the first and second anchors simultaneously to, for example, change the shape of one or both anchors. The device may include a lock adapted to lock the first and second anchors in their deployed configuration, and the lock may be adapted to unlock in response to an unlocking force from an unlocking actuator, such as a tether adapted to deliver a proximally directed unlocking force on the lock.

In some embodiments the actuator is a first actuator and the actuation element of the percutaneous mitral valve annuloplasty device is a first actuation element, and the deployment apparatus further includes a second actuator and the percutaneous mitral valve annuloplasty device further includes a second actuation element adapted to receive an actuation force from the second actuator and to transmit the second actuation force to the first and second anchors simultaneously. The first actuator (e.g., a tether) may be adapted to deliver a proximally directed actuation force and the first actuation element of the mitral valve annuloplasty device may be adapted to receive the proximally directed actuation force. The second actuator (such as a catheter) may be adapted to deliver a distally directed actuation force and the second actuation element of the mitral valve annuloplasty device may be adapted to receive the distally directed actuation force, the first and second actuation elements being adapted to move toward each other in response to the first and second actuation forces. The first and second actuation elements of the mitral valve annuloplasty device form a lock adapted to lock the first and second anchors in a deployed configuration.

In some embodiments the device includes an extension extending between the first anchor and the second anchor, with the connector being further adapted to move with respect to the extension in response to the first and second actuation forces. The extension and the connector may each communicate with the first anchor to change the first anchor's shape in response to relative movement between the extension and the connector.

Yet another aspect of the invention is a method of modifying the shape of a mitral valve annulus including the following steps: inserting a percutaneous mitral valve annuloplasty device into a coronary sinus adjacent to the mitral valve annulus, with the mitral valve annuloplasty device including a connector disposed between first and second anchors; and applying a distally or proximally directed actuation force to the mitral valve annuloplasty device to deploy the first and second anchors simultaneously, e.g., to change the shape of the first anchor or the first and second anchors. In some embodiments the mitral valve annuloplasty device includes a lock, the method further including the step of locking the first and second anchors in a deployed configuration. The method may also include the step of unlocking the first and second anchors, such as by applying a proximally directed force on the lock.

In some embodiments the actuation force is a first actuation force (such as a proximally directed force), with the method further including the step of applying a second actuation force (such as a distally directed force) to the mitral valve annuloplasty device to deploy the first and second anchors simultaneously.

In some embodiments the step of applying an actuation force includes moving a first actuation element of the mitral valve annuloplasty device toward a second actuation element of the mitral valve annuloplasty device. The method in this embodiment may also include locking the first and second actuation elements together to lock the anchors in a deployed configuration and moving the first and second actuation elements apart to unlock the anchors from the deployed configuration.

In some embodiments the applying step includes the step of applying a first actuation force, the method further including the steps of moving the second anchor proximally while the first anchor remains substantially in place within the coronary sinus and applying a second actuation force to further deploy the anchors.

Other aspects of the invention will be understood from the following detailed description.

BRIEF DESCRIPTION OF THE DRAWINGS

The invention, together with further aspects and advantages thereof, may best be understood by making reference to the following description taken in conjunction with the accompanying drawings, in the several figures of which like reference numerals identify identical elements, and wherein.

DETAILED DESCRIPTION OF THE INVENTION

Figure 1:
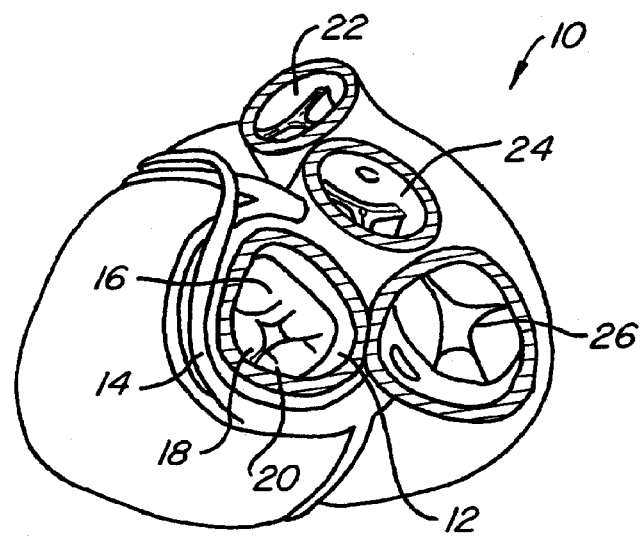
FIG. 1 is a superior view of a human heart with the atria removed.

Referring now to FIG. 1, it is a superior view of a human heart 10 with the atria removed to expose the mitral valve 12, and the coronary sinus 14 of the heart 10. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venous system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
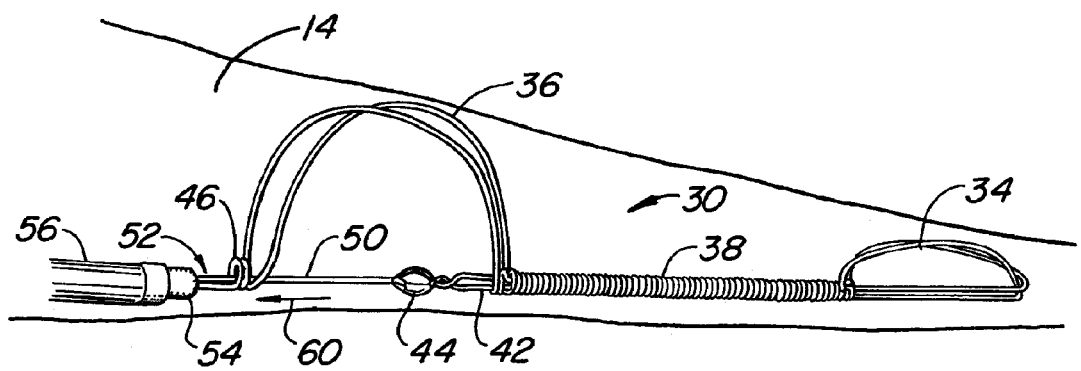
FIG. 2 is a perspective side view illustrating a mitral valve therapy device embodying the present invention during deployment or release.

FIG. 2 shows a percutaneous mitral valve annuloplasty device 30 embodying the present invention in the coronary sinus 14. As may be noted in FIG. 2, the device 30 includes a distal anchor 34, a connecting member 38, and a proximal anchor 36.

The anchors 34 and 36 and the connecting member 33 may be formed from the same material to provide an integral structure. More specifically, the device 30 may be formed of most any biocompatible material such as stainless steel or Nitinol, a nickel/titanium alloy of the type well known in the art having shape memory. Nitinol may be preferred for its shape memory properties.

As will be further noted from FIG. 2, the connecting member 38 is formed of a rigid coil having a central, longitudinal passage. Through this passage extends a locking extension 42 which extends through the passage from the distal anchor 34. The locking extension 42 forms part of a deployment mechanism which further includes a lock formed from a locking element 44 and an eyelet 46. The locking element 44 is arrowhead-shaped and is dimensioned to be lockingly received by the eyelet 46 as may be seen in FIG. 3.

The deployment mechanism is controlled by a pair of tethers including a first tether 50 and a second tether 52 which extend through an inner deployment catheter 54. Extending over the inner deployment catheter 54 is an outer deployment catheter 56. Tethers 50 and 52 and catheter 54 serve as percutaneous actuators for deploying device 30 to treat mitral valve regurgitation, repositioning device 30 within the coronary sinus, or removing device 30 from the patient.

Figure 3:
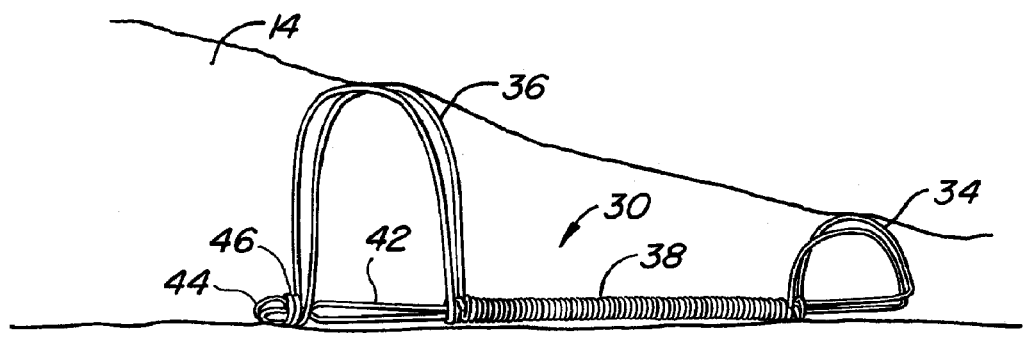
FIG. 3 is a perspective side view illustrating the device of FIG. 2 in a fully locked and deployed condition within the coronary sinus of a heart.

When the device 30 is to be deployed, a distally directed force is applied through the end of the inner catheter 54 as it is held against eyelet 46. The first tether 50, which is looped through the locking element 44, applies a proximally directed force to locking element 44, as indicated by arrow 60. This pulls the locking element 44 into and through the eyelet 46, and/or pushes eyelet 46 over locking element 44, depending on the relative movements of those elements. Once through the eyelet 46, the locking element 44 self-expands to remain locked by the eyelet 46 as seen in FIG. 3. As the locking element 44, and hence the locking extension 42, is pulled proximally, both the anchors 34 and 36 expand outwardly together and eventually anchor to the coronary sinus 14. The lock formed by locking element 44 and eyelet 46 helps maintain expansion of the anchors against the coronary sinus wall.

The relative sizes of anchors 34 and 36 may be chosen so that neither anchor is firmly lodged against the coronary sinus wall until the lock is locked. Alternatively, the distal anchor 34, proximal anchor 36 and connecting member 38 may be so dimensioned as to be able to anchor the distal anchor 34 in the coronary sinus before the locking element 44 is received by the eyelet 46. This would permit the device 30 to be pulled in a proximal direction after firm engagement of the distal anchor with the coronary sinus but before full deployment of the proximal anchor to cinch the coronary sinus and reshape the mitral valve annulus. The locking element 44 may then be pulled through the eyelet 46 to expand the anchors further to firmly lodge the proximal anchor against the coronary sinus wall and to lock the device in that position.

If after deployment, it is considered prudent to release the device 30 from the coronary sinus for, for example, removal or repositioning of the device 30, the second tether 52, which is looped through the eyelet 46, is pulled in the proximal direction. This causes the eyelet 46 to be pulled over and from the locking element 44. The locking extension 42 will spring back in a distal direction to cause the first anchor 34 and second anchor 36 to contract inwardly together and disengage the coronary sinus 14 together. In this manner, the device 30 is easily and readily released from the coronary sinus for removal or repositioning of the device 30.

The device may be formed from a single piece of Nitinol wire. First, the wire is folded in half to form a coextending wire pair. The wire pair is then coiled at one end to form the eyelet. Then, the wire pair is bent just distal of the eyelet to form the second anchor 36. The wire pair is then tightly coiled distal to the anchor 36 to form the rigidly coiled connecting member 36 having the central, longitudinal passage. Proximal the coiled connecting member 38, the wire pair is again bent to form the first anchor 34. The wire pair is then bent back from the distal anchor 34 and fed through the passage of the connecting member 38. Then the wire is twisted once to form the arrowhead-shaped locking element 44.

What is claimed is:

1. A method of modifying the shape of a mitral valve annulus comprising:
    inserting a percutaneous mitral valve annuloplasty device into a coronary sinus adjacent to the mitral valve annulus, the mitral valve annuloplasty device comprising a connector disposed between first and second anchors; and
    applying a distally or proximally directed actuation force to the mitral valve annuloplasty device to expand the first and second anchors simultaneously.

2. The method of claim 1 wherein the applying step comprises applying the actuation force to the mitral valve annuloplasty device to change the shape of the first anchor.

3. The method of claim 1 wherein the applying step comprises applying the actuation force to the mitral valve annuloplasty device to change the shape of the first and second anchors.

4. The method of claim 1 wherein mitral valve annuloplasty device comprises a lock, the method further comprising locking the first and second anchors in a expanded configuration.

5. The method of claim 4 further comprising unlocking the first and second anchors.

6. The method of claim 5 wherein the unlocking step comprises applying a proximally directed force on the lock.

7. The method of claim 1 wherein the actuation force is a first actuation force, the method further comprising applying a second actuation force to the mitral valve annuloplasty device to expand the first and second anchors simultaneously.

8. The method of claim 7 wherein the step of applying a first actuation force comprises applying a proximally directed force to a first actuation element of the mitral valve annuloplasty device.

9. The method of claim 8 wherein the step of applying a second actuation force comprises applying a distally directed force to a second actuation element of the mitral valve annuloplasty device.

10. The method of claim 1 wherein the applying step comprises applying the actuation force to the mitral valve annuloplasty device to move a first actuation element of the mitral valve annuloplasty device toward a second actuation element of the mitral valve annuloplasty device.

11. The method of claim 10 further comprising locking the first and second actuation elements together to lock the anchors in the expanded configuration.

12. The method of claim 11 further comprising moving the first and second actuation elements apart to unlock the anchors from the expanded configuration.

13. The method of claim 1 wherein the applying step comprises applying a first actuation force, the method further comprising moving the second anchor proximally while the first anchor remains substantially in place within the coronary sinus and applying a second actuation force to further expand the anchors.

* * * * *